(12) United States Patent
Reinhardt

(10) Patent No.: US 7,037,286 B1
(45) Date of Patent: May 2, 2006

(54) WRIST BRACE

(75) Inventor: James W. Reinhardt, Seattle, WA (US)

(73) Assignee: Tannhauser Gate LLC, Seattle, WA (US)

( * ) Notice: Subject to any disclaimer, the term of this patent is extended or adjusted under 35 U.S.C. 154(b) by 0 days.

(21) Appl. No.: 10/974,169

(22) Filed: Oct. 26, 2004

(51) Int. Cl.
*A61F 5/00* (2006.01)

(52) U.S. Cl. ............... 602/21; 602/20; 602/5; 602/64; 128/878; 128/879

(58) Field of Classification Search ............ 602/5, 602/16, 20, 21, 64; 2/16, 162, 910; 128/878–879; 473/59, 62, 213; D29/113–120.1; D24/189–190; 482/44–46
See application file for complete search history.

(56) References Cited

U.S. PATENT DOCUMENTS

| | | | | |
|---|---|---|---|---|
| 704,579 A * | 7/1902 | Rollason | ................. | 2/162 |
| 3,170,460 A * | 2/1965 | Stilson | ................. | 602/22 |
| 4,191,373 A * | 3/1980 | Lancellotti | ................. | 602/16 |
| 4,768,502 A * | 9/1988 | Lee | ................. | 602/6 |
| 4,854,310 A * | 8/1989 | Lee | ................. | 602/21 |
| 5,056,504 A * | 10/1991 | Mann | ................. | 601/40 |
| 5,409,451 A * | 4/1995 | Daneman | ................. | 602/21 |
| 5,624,388 A * | 4/1997 | Lehr | ................. | 602/20 |
| 5,713,836 A * | 2/1998 | O'keefe | ................. | 602/5 |
| 5,836,902 A * | 11/1998 | Gray | ................. | 602/5 |
| 5,868,692 A | 2/1999 | Michniewicz | | |
| 5,888,174 A * | 3/1999 | Schlee | ................. | 482/44 |
| 6,049,905 A * | 4/2000 | Owens | ................. | 2/16 |
| 6,102,880 A * | 8/2000 | Nelson et al. | ................. | 602/21 |
| 6,436,031 B1* | 8/2002 | Salib | ................. | 600/39 |
| 6,685,662 B1* | 2/2004 | Curry et al. | ................. | 602/20 |
| 2004/0019306 A1* | 1/2004 | Brewer | ................. | 602/21 |

\* cited by examiner

*Primary Examiner*—Henry Bennett
*Assistant Examiner*—Amanda Wieker
(74) *Attorney, Agent, or Firm*—Speckman Law Group PLLC; Janet Sleath

(57) ABSTRACT

The present application discloses an open air wrist brace for use in supporting the wrist in an anatomically neutral position, or in a position that permits therapeutically-useful extension, without increasing pressure on the carpal tunnel, median nerve or flexor tendons in the forearm.

21 Claims, 6 Drawing Sheets

WRIST BRACE

FIELD OF THE INVENTION

The present invention relates to wrist braces, and more specifically, to an open air wrist brace for use in supporting the wrist in an anatomically neutral position or in a position that permits therapeutically-useful extension, without increasing pressure on the carpal tunnel, median nerve or flexor tendons in the forearm.

BACKGROUND

Many people suffer from compression injury to the soft tissues of the wrist and carpal tunnel. These injuries may be produced in the workplace, e.g., by frequent, sustained repetitive motions involving the use of the hands, or may be associated with trauma to the hand or wrist, pre-existing medical conditions, hormonal changes, hereditary traits, and use of medical apparatus such as wheelchairs, and other factors (Gross et al, 2002). Without treatment, such injuries accumulate and lead to chronic neuromuscular disorders of the hand and the upper limb. The most familiar of these disorders is carpal tunnel syndrome, which is a growing public health issue that affects approximately 0.1% of the U.S. population (Hunter, Mackin and Callahan, *Rehabilitation of the Hand and Upper Extremity*. Fifth Edition, Mosby press, USA, 2002) and produces pain, discomfort, nerve conduction disturbances and impairment of function of the hand and sometimes the upper limb as well.

Carpal tunnel syndrome is caused by compression of the median nerve in the carpal tunnel. The median nerve receives blood, oxygen and nutrients through a microvasculature network which is present in the connective tissue surrounding the nerve fiber. An increased pressure on the nerve fiber constricts the microvessels and reduces the blood flow to the nerve. Prolonged deprivation of oxygen and nutrients will result in severe nerve damage.

The carpal tunnel is a confined anatomic space defined by the transverse carpal ligament on the palmar (anterior) side of the hand and by a semicircular bony ledge comprised of the carpal wrist bones on the dorsal and lateral sides of the hand. The tunnel serves as a conduit for the median nerve, blood vessels, and tendons which supply the extrinsic hand muscles.

An increase in the volume of the carpal contents or a decrease in the cross-sectional area of the carpal tunnel will increase the hydrostatic (interstitial) pressure in the tunnel and can potentially lead to compression damage to the median nerve. For example, conditions that irritate or inflame the tendons can cause them to swell and exert pressure on the median nerve. The increase in volume of the tendons and the median nerve, when inflamed, can increase the likelihood of carpal tunnel symptoms. A thickening of the transverse carpal ligament or of the bones a butting the carpal tunnel can reduce cross-sectional area of the tunnel. The tunnel cross-sectional area also changes with wrist position. Wrist flexion or extension decreases the cross-sectional area, and increases the hydrostatic pressure of the tunnel. Most wrist flexion occurs around the lateral axis of the radiocarpal joint, whereas most wrist extension occurs around the lateral axis of the midcarpal joint. Wrist flexion causes the flexor tendons to rearrange so they are more likely to compress the median nerve. The median nerve responds by rearranging its position between the superficial flexor tendons (Skie et al, J. Hand Surgery [Am] 15: 934–939 (1990)). The carpal tunnel cross-sectional area is smaller in carpal tunnel syndrome patients compared with asymptomatic control populations.

Carpal tunnel syndrome may be treated by non-surgical and surgical means. In early stages of development, therapies are directed to alleviating symptoms and preventing the occurrence of more severe symptoms. Such therapies include: restricting the motion of the wrist by means of wrist braces and splints, controlling swelling of soft tissue structures by administering anti-inflammatory medications, sometimes injecting steroids locally into the carpal tunnel; applying heat or cold to the affected site to promote repair of injured tissues; providing exercises to increase circulation, speed recovery and increase the range of motion of the wrist; and avoiding activities that produced the symptoms initially. Surgery, which may involve cutting the transverse carpal ligament to relieve pressure on the median nerve, may be necessary if the symptoms are severe and/or if the non-surgical therapies do not resolve the problem. Non-surgical therapies are reported to be effective in relieving symptoms of 86% of afflicted patients (Benefice, 1994).

The present invention is drawn to wrist brace technology for use by patients with existing carpal tunnel syndrome and related nerve entrapment disorders, and patients who are at risk for developing carpal tunnel syndrome and are in need of wrist support which allows motion of the fingers and palm.

The prior art wrist braces have one or more of the following drawbacks. They confine the wrist and forearm in a neutral position, but restrict the motion of the fingers required for daily activities; they enclose the hand, wrist and forearm in material which prevents air from circulating to the underlying tissues and promotes accumulation of moisture, bacteria and dirt between the brace and the tissue; they are difficult to attach to the hand and bulky to wear under clothing; they exert pressure on flexor tendons and the median nerve; and if made from a rigid material, they are uncomfortable to wear, develop unpleasant odors and have an anatomically incorrect shape.

U.S. Pat. No. 6,540,710 discloses a one piece molded plastic wrist brace that is designed to hold the wrist in a neutral position, block wrist flexion, extension, and ulnar/radial deviations, and limit hand movement without compressing the anterior forearm and flexor tendons.

SUMMARY OF THE INVENTION

The present invention provides an open air wrist brace that is lightweight, durable, and easily attached by the wearer in a single motion, and is designed to hold the wrist in a neutral position, or in a position that prevents flexion but permits therapeutically-useful extension, without restricting the wearer's use of the hand to grasp objects and to perform daily tasks. The brace is held in place without exerting pressure on the carpal tunnel, or on tendons or nerves of the wrist and forearm.

DETAILED DESCRIPTION

The invention provides an open air wrist brace for holding the user's hand in an anatomically neutral position while allowing the use of the hand and fingers for manual tasks. The term "anatomically neutral position" as used herein means 2 degrees±9 degrees of flexion and 1 degree±9 degrees of ulnar deviation. A wrist brace that holds the user's wrist and hand in an anatomically neutral position is useful as an initial treatment for subjects with symptoms of carpal tunnel syndrome and median nerve irritation, as well as for preventing these conditions in at-risk individuals.

The invention additionally encompasses an open air wrist brace for restraining the hand in a position of at least 10 degrees to about 30 degrees of extension while preventing flexion, as may be required as a post-operative treatment, for example, where a certain degree of extension is desirable for recovery. Thus the brace restrains the hand in a position of at least 10 degrees, at least 15 degrees, at least 20 degrees, at least 25 degrees, or about 30 degrees of extension.

The brace is formed from a substantially rigid, lightweight material, preferably a moldable, durable, hypo-allergenic plastic or reinforced plastic, and is preferably lined with a material, such as foam rubber, that provides a non-abrasive cushion between the brace and the skin. The term "substantially rigid" is used herein to mean a supportive brace that resists a change in shape during performance of manual tasks. The open air brace is designed to provide ventilation to the hand and wrist by leaving uncovered the fingers, palm, wrist and a triangular portion of the dorsal surface of the hand.

The brace rests on the outside of the user's hand and is held in place by hand tabs which turn onto the palmar surface beneath the metarcarpal-phalangeal joints of the forefinger and fifth finger thus allowing free motion of the thumb and fingers, and by posterior struts which grip the sides of the forearm without compressing muscles, tendons or nerves on the underside of the forearm and wrist. In a preferred embodiment, the posterior struts are secured with a strap fastener made of a soft non-rigid material, e.g., Velcro@, or an easily stretchable rubber, e.g., neoprene, or an elastic fiber blend (e.g., Spandex blend).

The brace is particularly useful for persons at risk for, or suffering from, tendonitis, carpal tunnel syndrome and repetitive stress injuries resulting in median nerve entrapment. These and other advantages of the present invention will be apparent from the description and drawings that follow. The drawings illustrate various preferred embodiments of the invention and are not intended to limit the scope of the invention as claimed.

Figure 1:
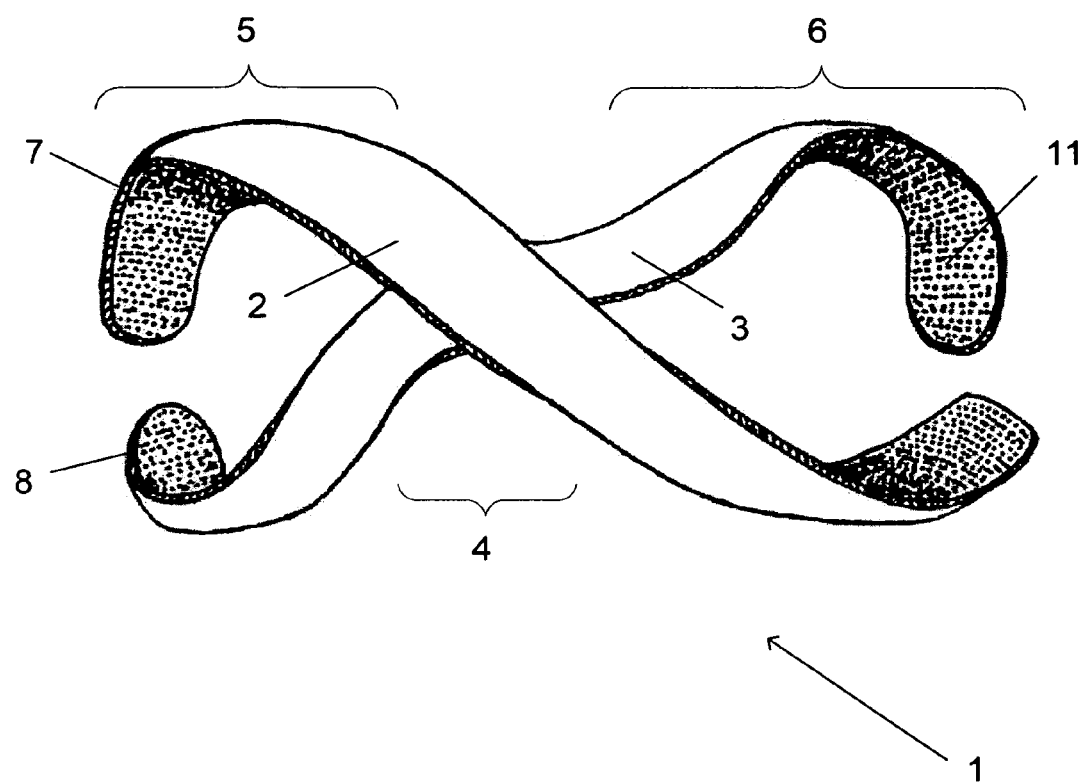
FIG. 1. Top view of wrist brace without straps.

Generally, as shown in FIG. 1, the wrist brace 1 comprises a double helical skeleton formed from two helical-shaped struts 2 and 3 which interconnect in a crossover region 4 and continue anteriorly and posteriorly to form an anterior portion 5 and a posterior portion 6. In the anterior portion 5, the struts end in hand tabs 7 and 8. A non-abrasive liner 11 is also shown in FIG. 1, and in FIGS. 2B, 2C and 4 below.

The helical struts can be connected in several different ways, to accommodate different clinical needs and consumer preferences (FIG. 2, panels A, B and C).

Figure 2A:
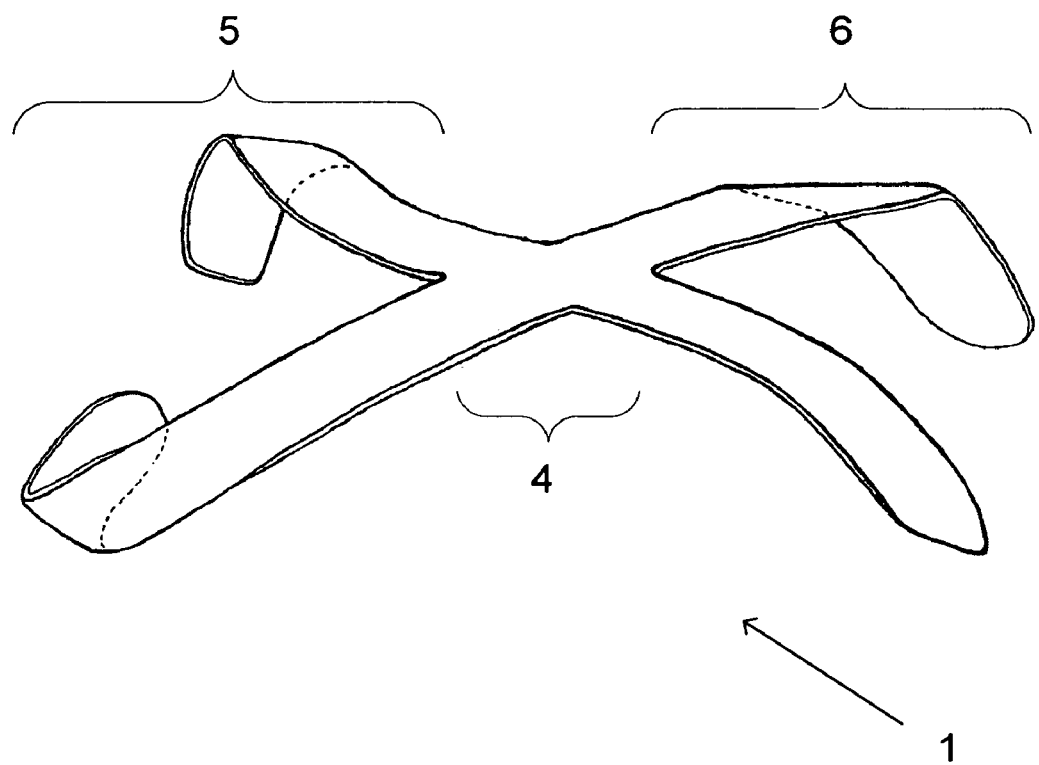
FIG. 2. Top view of wrist brace worn by user: A. non-pivotable attachment; B. pivotable attachment; C. spring mechanism attachment.

The helical struts can be connected in nonpivotable manner, as exemplified in FIG. 2A. This embodiment may be preferred, for example, for a custom-made wrist brace that is molded for a particular user, according to the user's wrist and forearm dimensions. The custom-made brace may be manufactured as a unitary piece comprising the anterior portion, the posterior portion and the crossover region, or alternatively, as two separate helical pieces which are connected in a crossover region that is predetermined for the user.

Figure 2B:
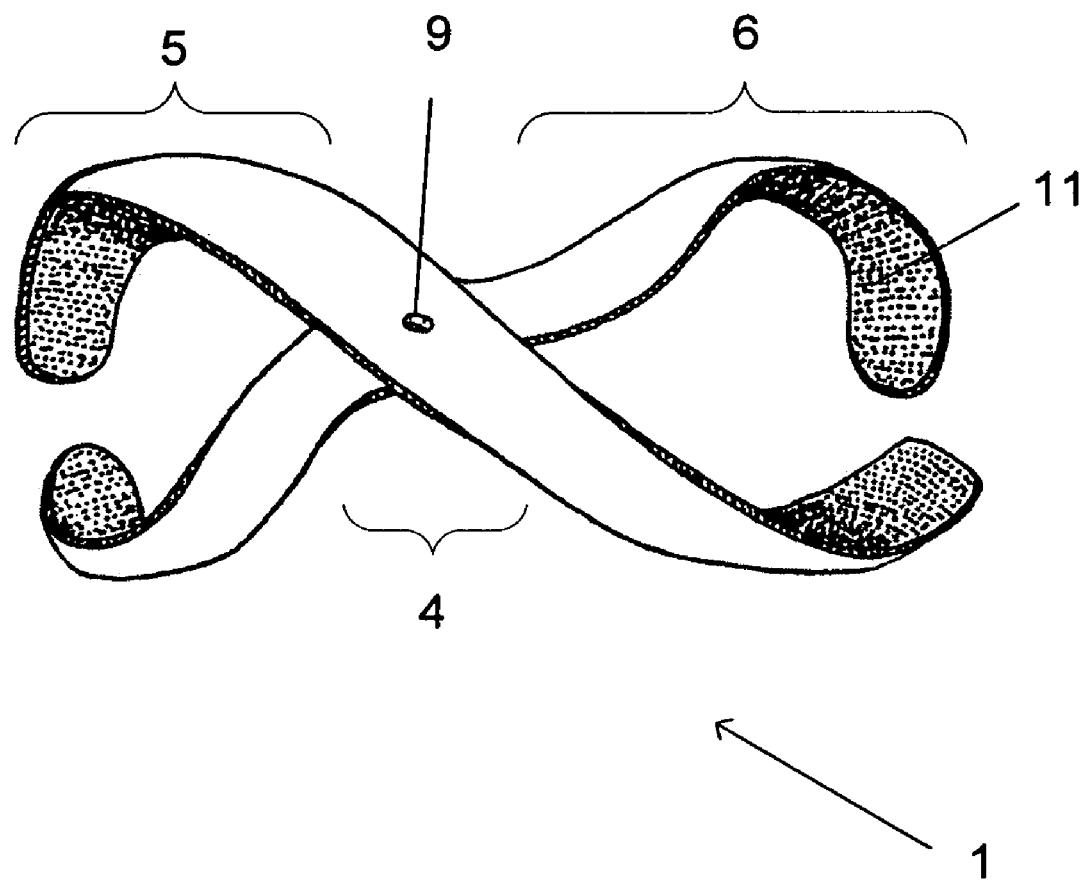

In a particularly preferred embodiment of the wrist brace, shown in FIG. 2B, a pivot means 9 is used to connect the helical struts in a pivotable manner, thus allowing the wearer to adjust the width of the anterior portion to the size of the wearer's hand.

Figure 2C:
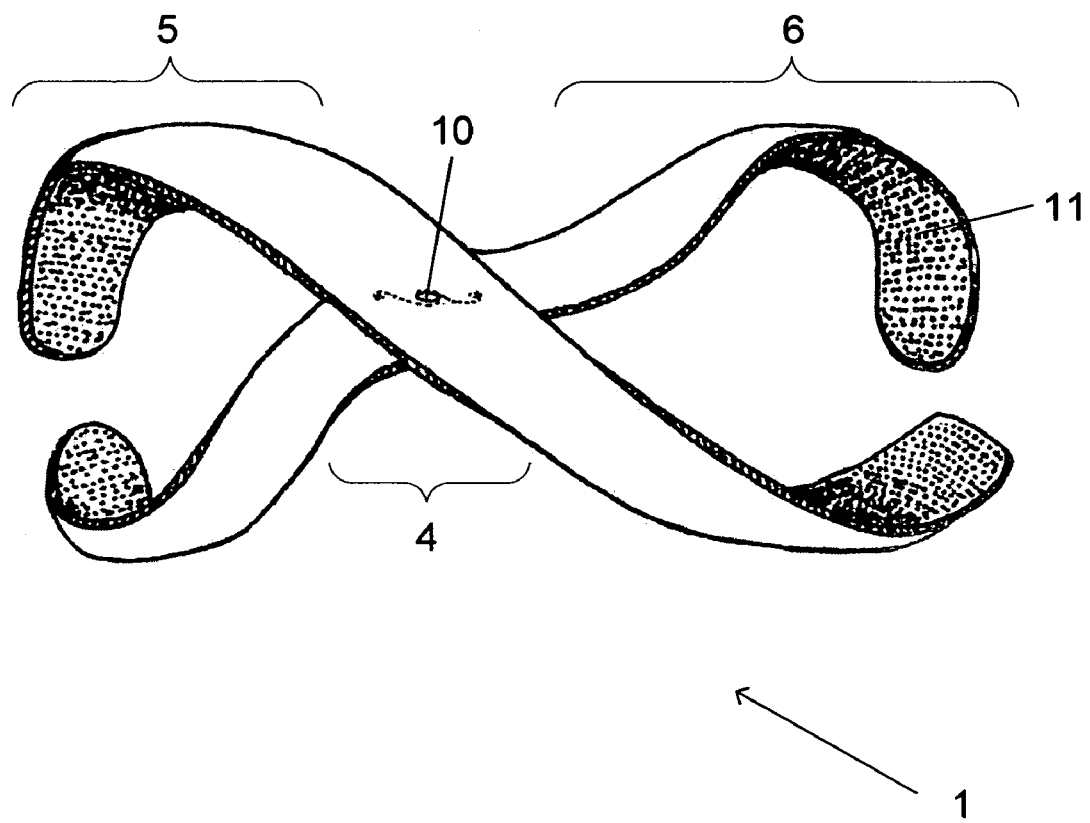

In yet another embodiment, shown in FIG. 2C, the helical struts are connected by a spring mechanism 10.

Figure 3A:
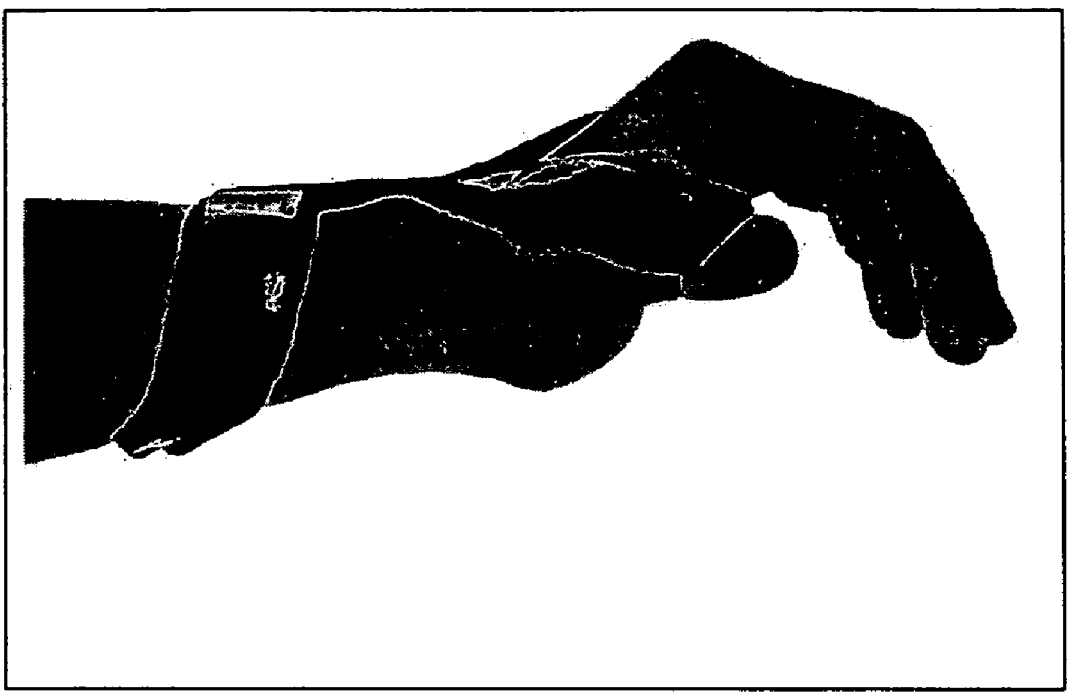
FIG. 3. A wrist brace embodiment worn by user. A. Side view; B. Top view.

FIG. 3 shows a side view and a top view of a wrist brace embodiment worn by the user.

Figure 3B:
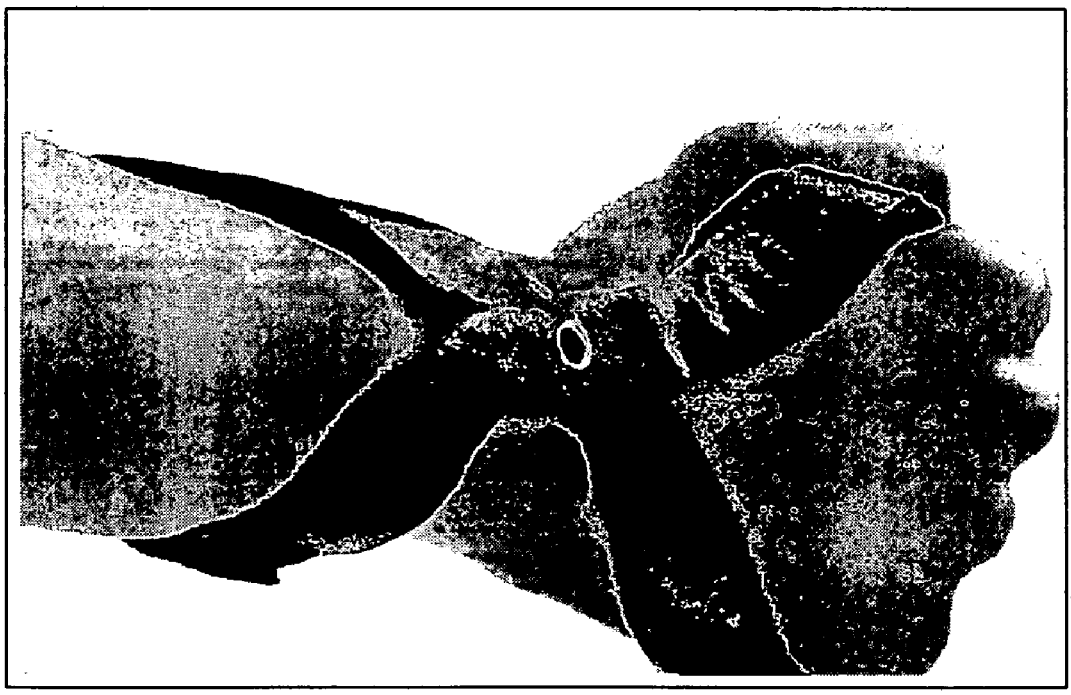

Generally, as shown in FIG. 3B, the helical struts intersect in the vicinity of the midcarpal and radiocarpal joints between the ulna and radial styloids on the back of the wrist, thereby avoiding contact with the median nerve or tendons associated with the movement of the hand and wrist.

Figure 4:
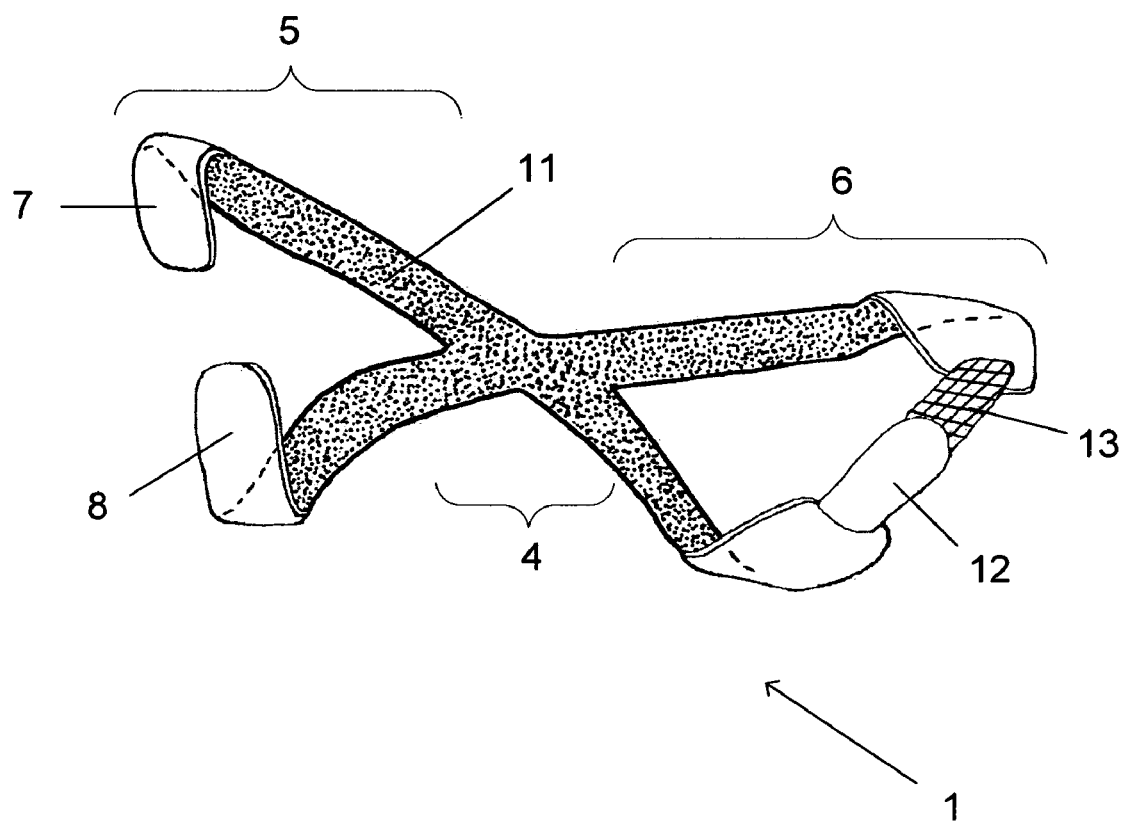
FIG. 4. View of underside of wrist brace embodiment showing hand tabs, liner and strap fastener.

The posterior portion of the wrist brace 6 (shown specifically in FIGS. 1 and 4) attaches the brace noncompressively to the forearm. In one preferred embodiment, the struts in the posterior portion are connected to each other by a strap fastener 12 with a Velcro attachment 13 (FIG. 4). FIG. 4 is a view of the underside of this embodiment specifically pointing out hand tabs, liner and strap fastener. Those of ordinary skill in the art will recognize that other strap fastening means are known in the art, and the arrangement shown in FIG. 4 is intended to exemplify one such means. As described above, the strap fastener can also be made from stretchable materials.

In another preferred embodiment of the invention, the wrist brace is held in place mainly by the imposition of an inward pressure on the hand and forearm, e.g., via the action of a spring mechanism connecting the helical struts (see FIG. 2C). The posterior struts rest firmly on the bones and muscle at the sides of the forearm.

In yet another preferred embodiment, the wrist brace is custom-made to the dimensions of the user's hand and forearm such that the posterior struts conform to the sides of the forearm. As disclosed above and illustrated in FIG. 2A, the helical struts can be connected in a non-pivotable manner.

The above embodiments can be manufactured in small, medium or large hand sizes. The pivot may be made adjustable to accommodate hands of different thicknesses as well.

Materials and Methods of Manufacture

The wrist brace disclosed in this application can be custom-made for a particular user or mass-manufactured. Those skilled in the art will know of materials and methods of manufacture in addition to than those described below.

A heat-moldable plastic is a preferred material for use in constructing a custom-made wrist brace. Such material can be conveniently molded directly on the wrist and hand of the intended wearer to obtain a custom-fit. Where cost is not a consideration, carbon fiber may be a preferred material for a custom-made wrist brace. An exemplary method of manufacture is to form a mold of the user's arm, wrap the carbon fiber-reinforced tape around the cast to the desired thickness and shape of the brace, and subject the tape to curing conditions.

For mass manufacturing, the wrist brace is preferably constructed of a non-metallic synthetic material, or a composite material that is lightweight, strong, easily moldable, durable, impact resistant, temperature resistant, and maintains its shape under pressures that the user would typically be exposed to in performing everyday manual tasks.

Examples of materials that are suitable for use include thermoplastics, such as polycarbonate and polycarbonate blends; composites, such as carbon-fiber reinforced plastics; and polyamides. Methods for mass-manufacturing braces formed from these materials are well-known in the art, and include, for example, two-piece plastic injection molding, co-molding plastic with rubber inserts, and others.

While the present invention has been described with reference to the specific embodiments thereof, it should be understood by those skilled in the art that various changes may be made and equivalents may be substituted without departing from the true spirit and scope of the invention.

For example, a single helical strut can be formed into a double helical wrist brace having an anterior loop portion that supports the metacarpal-phalangeal joints of the forefinger and fifth finger, with a crossover region on the palm of the hand, and a posterior portion formed by a second crossover region on the top side of the forearm between the radial and ulnar styloids, and a strap fastening means. Such a wrist brace would function in an equivalent manner and produce similar results as the embodiments claimed herein. Similarly, a wrist brace with a single tab supporting all of the metacarpal-phalangeal joints of the hand would be considered to be an equivalent of a brace with two separate hand tabs.

The wrist brace of the present invention could also be modified such that the two posterior limbs could be replaced with a single posterior limb and a fastening means.

In addition, many modifications may be made to adapt a particular situation, material, composition of matter, method, method step or steps, for use in practicing the present invention. The wrist brace embodiments of the present invention may be designed with fashion in mind, e.g., the braces can be made from clear plastic of different colors, and may optionally include watches, colors, designer fabrics, and the like. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

I claim:

1. A wrist brace comprising an open air skeleton formed by two continuous substantially rigid helical struts which cross each other and interconnect within a crossover region to form two anterior limbs, an X-shaped trunk region and two posterior limbs, wherein the ends of said anterior limbs are shaped to form hand engaging means and said anterior limbs cooperate to secure the brace on the hand of the wearer and the ends of said posterior limbs comprise forearm engaging means.

2. The wrist brace of claim 1, wherein the brace supports the user's hand and wrist in an anatomically neutral position.

3. The wrist brace of claim 1, wherein the brace restrains the hand in a position of about 10 degrees to about 30 degrees of extension.

4. The wrist brace of claim 1, wherein the hand engaging means comprise tabs that support the hand below the joints of at least the second and fifth fingers on the palmar surface of the hand.

5. The wrist brace of claim 1, wherein the forearm engaging means comprise strut ends that rest securely on the bones of the forearm at the sides of the forearm.

6. The wrist brace of claim 1, wherein the forearm engaging means are connected by a strap fastener.

7. The wrist brace of claim 1, wherein the helical struts are non-pivotable.

8. The wrist brace of claim 1, wherein the skeleton comprises a thermoplastic material.

9. The wrist brace of claim 8, wherein the thermoplastic material is polycarbonate or a polycarbonate blend.

10. The wrist brace of claim 1, wherein the skeleton comprises carbon fiber material.

11. The wrist brace of claim 1, further comprising a non-abrasive liner.

12. The wrist brace of claim 11, wherein the liner is foam rubber.

13. The wrist brace of claim 1, wherein the wrist is supported in a neutral position when worn by the user.

14. The wrist brace of claim 1, wherein the substantially rigid helical struts cross each other and interconnect within a single crossover region.

15. A wrist brace comprising an open air skeleton formed by two continuous substantially rigid helical struts which cross each other and interconnect within a crossover region to form two anterior limbs, an X-shaped trunk region and two posterior limbs, wherein the ends of said anterior limbs comprise hand engaging means, said anterior limbs cooperate to secure the brace on the hand of the wearer, the ends of said posterior limbs comprise forearm engaging means, and the helical struts are pivotable.

16. The wrist brace of claim 15, wherein the helical struts are connected by a pivot means.

17. The wrist brace of claim 15, wherein the skeleton is formed from a material selected from the group consisting of: thermoplastic materials; and carbon fiber materials.

18. The wrist brace of claim 15, further comprising a non-abrasive liner.

19. A wrist brace comprising an open air skeleton formed by two continuous substantially rigid helical struts which cross each other and interconnect within a crossover region to form two anterior limbs, an X-shaped trunk region and two posterior limbs, wherein the ends of said anterior limbs comprise hand engaging means, said anterior limbs cooperate to secure the brace on the hand of the wearer, the ends of said posterior limbs comprise forearm engaging means, and the helical struts are connected by a spring mechanism.

20. The wrist brace of claim 19, wherein the skeleton is formed from a material selected from the group consisting of: thermoplastic materials; and carbon fiber materials.

21. The wrist brace of claim 19, further comprising a non-abrasive liner.

* * * * *